(12) United States Patent
Simon

(10) Patent No.: US 9,429,529 B2
(45) Date of Patent: Aug. 30, 2016

(54) DEVICE FOR NEUTRON IMAGERY IN IMMERSION AND IMAGING METHOD USING SAID DEVICE

(71) Applicant: COMMISSARIAT A L'ENERGIE ATOMIQUE ET AUX ENERGIES ALTERNATIVES, Paris (FR)

(72) Inventor: Eric Simon, Pertuis (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/359,871

(22) PCT Filed: Nov. 21, 2012

(86) PCT No.: PCT/EP2012/073236
§ 371 (c)(1),
(2) Date: May 21, 2014

(87) PCT Pub. No.: WO2013/076142
PCT Pub. Date: May 30, 2013

(65) Prior Publication Data
US 2014/0361179 A1      Dec. 11, 2014

(30) Foreign Application Priority Data

Nov. 22, 2011 (FR) ...................... 11 60623

(51) Int. Cl.
| | |
|---|---|
| G01N 23/05 | (2006.01) |
| G01T 3/06 | (2006.01) |
| G01N 23/04 | (2006.01) |
| C09K 11/02 | (2006.01) |
| C09K 11/77 | (2006.01) |
| G21K 4/00 | (2006.01) |

(52) U.S. Cl.
CPC ............... *G01N 23/05* (2013.01); *C09K 11/02* (2013.01); *C09K 11/77* (2013.01); *C09K 11/7789* (2013.01); *G01N 23/043* (2013.01); *G01T 3/06* (2013.01); *G21K 4/00* (2013.01); *G01N 2223/625* (2013.01)

(58) Field of Classification Search
CPC .......... G21K 4/00; G01N 23/05; G01T 3/00; G01T 3/06
USPC ..................................... 250/390.01
See application file for complete search history.

(56) References Cited

U.S. PATENT DOCUMENTS

| | | | |
|---|---|---|---|
| 3,436,538 A * | 4/1969 | Basdekas | 376/159 |
| 3,891,852 A | 6/1975 | Bollen et al. | |
| 5,635,727 A * | 6/1997 | Niimura et al. | 250/583 |
| 2003/0155530 A1 | 8/2003 | Adnani et al. | |
| 2004/0104356 A1* | 6/2004 | Bross et al. | 250/486.1 |
| 2005/0208290 A1* | 9/2005 | Patel | 428/323 |
| 2010/0193695 A1* | 8/2010 | Yeow et al. | 250/370.07 |

FOREIGN PATENT DOCUMENTS

DE      19644522 A1      5/1998

* cited by examiner

*Primary Examiner* — Yara B Green
(74) *Attorney, Agent, or Firm* — Baker & Hostetler LLP

(57) ABSTRACT

A device designed to be used for neutron imaging, immersed in a medium containing specimens to be analyzed, comprises a first converter comprising a first material capable of converting thermal neutron radiation into remnant beta radiation and a second converter comprising a second material capable of converting a remnant beta radiation into light radiation, the second converter being in contact with the first converter. A method is also provided for neutron imaging immersed in a medium and using the device.

10 Claims, 2 Drawing Sheets

DEVICE FOR NEUTRON IMAGERY IN IMMERSION AND IMAGING METHOD USING SAID DEVICE

CROSS-REFERENCE TO RELATED APPLICATIONS

This application is a National Stage of International patent application PCT/EP2012/073236, filed on Nov. 21, 2012, which claims priority to foreign French patent application No. FR 1160623, filed on Nov. 22, 2011, the disclosures of which are incorporated by reference in their entirety.

FIELD OF THE INVENTION

The field of the invention is that of the non-destructive testing of irradiating objects using neutronographic imaging.

BACKGROUND

Neutronography is a technique for non-destructive testing analogous in its principle to radiography using X-rays. A conditioned beam of neutrons from a source is used to supply an image by transparency of the object being examined.

A conventional neutronography installation is represented schematically in FIG. 1 which shows: a source of neutrons $S_N$ placed in a moderator medium, designed to reduce the energy of the neutrons that are produced. The entry window of a collimator C, which conditions the beam, is disposed at a calculated distance from this source. In this figure, a collimator with a divergent shape is shown. The collimator is equipped with a filter F made of a material designed to act as a barrier to the gamma radiation that can accompany the neutron transmission. The collimator comprises internal walls absorbing neutrons and a filling gas transparent to neutrons. At the exit of the collimator, the neutrons interact with the object under examination Ob, are transmitted through the latter and are absorbed by a detector $D_{ect}$ for forming the image. The use of a moderator element is indeed necessary given that, in general, the neutron sources emit a spectrum of fast neutrons which is very rarely suitable for imaging. The neutrons then need to be slowed down in a medium referred to as moderator surrounding the fast source. This method unfortunately leads to considerable losses in intensity because the moderator is not totally transparent to the neutrons and spurious captures are always taking place within it. In the moderator, the neutrons are slowed by successive collisions accompanied by transfers of energy to the atoms of the medium.

The object thus analyzed and traversed by a neutron flux generates an image that is specific to it. Indeed, the interaction of the neutrons within the material is characterized by scattering and absorption phenomena. The neutrons have, in particular, the capacity to detect atoms of hydrogen in media through metal structures, and the analysis can be undertaken by the spatial and temporal attenuation of the beam of neutrons.

Research nuclear reactors, producers of very high neutron fluxes, are the installations that are best placed for producing neutronographies of very high quality. In fact, they occupy a very important place amongst the installations dedicated to production non-destructive testing.

Since neutrons are indirectly ionizing particles, their direct detection is quite difficult. In order to overcome this handicap, in the detector, a material with a very large cross-section (probability of interaction) for neutron capture is used in order to obtain a high efficiency, this capture being accompanied by a secondary transmission of ionizing particles that can excite conventional detectors: photographic films, scintillators (material which emits light following the interaction with ionizing radiation (photon or charged particle)). Indeed, the light from scintillation is produced not only by absorption but also by other types of interactions with ionizing radiation such as scattering, for example.

In the nuclear field, two types of neutronography installations exist: neutronography in the reactor fuel pond, in which the imaging system is installed as close as possible to the core of the reactor right inside the pond (the system is immersed, which is for example the case of the OSIRIS neutronography system in France or the HFR at Petten in the Netherlands) and neutronography outside the reactor, in which the beam of neutrons is extracted from the reactor in order to form a beam exiting from the reactor fuel pond (the ORPHEE neutronography system for example).

OSIRIS is an experimental reactor with a thermal power of 70 megawatts. This is a light-water pond type of reactor with an open core whose main goal is to carry out testing and to irradiate fuel elements and structural materials for high power nuclear electrical plants with a high flux of neutrons and also to produce radioelements.

In the case of the examination of irradiated fuel elements, the appropriate neutronography system is immersed neutronography, for obvious reasons associated with the irradiating nature of the object under examination.

The severe constraint associated with this type of neutronographic imaging immersed in a reactor fuel pond of highly-irradiating objects is linked to the type of detector used to form the neutronographic image. Owing to the radioactive environment, the system must be insensitive to gamma radiation so as only to conserve the useful signal (interactions with the thermal neutrons). Currently, the device used in the framework of OSIRIS for performing the neutronographic analysis and installed on the bed of the pond is composed of three main parts:
  a pyramidal collimator whose apex is slightly truncated where an aluminum alloy plate is placed forming the entry field for the neutrons;
  at the rear of the collimator is located the chamber which receives the object to be examined;
  the support situated at the rear of the chamber receives a metal cassette containing a converter capable of converting a neutron flux into β radiation. The cassette provides a function of isolation vessel with respect to the neutron converter designed to be immersed during the irradiation phase.

The whole assembly is mobile and moves forward or backward toward or away from the core of the reactor. The technique is referred to as a transfer technique because the radiographic image is obtained following two consecutive sequences:
  the irradiation of the converter;
  the exposure of a photographic film after transferring the cassette outside of the pond in order to image the β radiation activity of the converter.

This method allowing only the neutron signal to be conserved is thus founded on a production of the image in two steps, after a transfer of a part of the system outside of the reactor fuel pond: an activatable converter is exposed to the neutron flux downstream of the object being inspected, then this converter is transferred outside of the pond in order to image its activity (beta activity), which supplies an image in transmission of the neutron absorption of the object being inspected. It offers the advantages of being able to test an object directly in the neighborhood of the core without removing it from the pond and of being able to image highly radioactive objects because the photographic film is never in the neighborhood of the latter. Thus, the irradiated fuel rods in an experimental device OSIRIS can be subjected to a neutronography before and after irradiation which allows the modifications of the state of the fuel and the effect of the irradiation to be seen.

Nevertheless, the systems enabling the production of neutronographic images under these conditions require the employment of a system that is transferable outside of the reactor fuel pond of the irradiation cassette type composed of aluminum alloy or other (activatable) metal material. The activation of this cassette imposes severe constraints on the measurement process (feedback from OSIRIS experiment): handling times, dosimetry for the operator.

Furthermore, the methods for neutronography by transfer currently employed impose the application of a primary converter for converting neutrons into remnant beta radiation, on a second system allowing the image to be produced (radiographic film or radio-luminescent storage screen), involving the necessity of bringing the two elements into the most perfect contact possible in order to optimize the resolution of the image (use of a vacuum box, etc.) and many handling operations by the operator.

SUMMARY OF THE INVENTION

It is for this reason, and in a more general context of testing by non-destructive means of irradiating objects and using neutronographic imaging, that one subject of the present invention is a novel type of device designed to be immersed for carrying out operations for non-destructive testing by an improved neutron imaging of specimens and notably of irradiated nuclear fuels.

The present invention can advantageously relate to immersed neutronography in a reactor fuel pond (notably aimed at an application to the future neutronography system of the RJH reactor) by providing a device allowing a high-resolution neutronographic image to be obtained, in an environment with a high neutron flux and high gamma flux, in a reactor fuel pond, using a system transferable outside of the pond, while guaranteeing a minimum activation of the associated structures so as to ensure the best radioprotection of the operator handling said transferred imaging system.

More precisely, a first subject of the present invention is a device designed to be used for neutron imaging immersed in a medium containing specimens to be analyzed, characterized in that it comprises a first converter comprising a first material capable of converting neutron radiation into remnant beta radiation and a second converter comprising a second material capable of converting a remnant beta radiation into light radiation, said second converter being in permanent contact with said first converter.

According to one variant of the invention, said device furthermore comprises a support comprising hydrogenated species on which said first and second converters are positioned, said support being transparent to light radiation.

According to one variant of the invention, the first material comprises dysprosium.

According to one variant of the invention, said second converter comprises a scintillator material which is a compound containing gadolinium which can be of type $Gd_2O_2S$ (Tb) (which can be doped with terbium).

According to one variant of the invention, the scintillator material is mixed with an organic binder.

According to one variant of the invention, the thickness of the first converter is of the order of a hundred microns.

According to one variant of the invention, the thickness of the second converter is of the order of ten microns.

According to one variant of the invention, the transparent support comprising hydrogenated species is of the polymethylmethacrylate type, which can have a thickness of the order of a few millimeters.

A second subject of invention is a leak-tight system comprising a vessel leak-tight to said medium, incorporating the device according to the invention.

According to one variant of the invention, the vessel is made of a material with low activation by a neutron flux, which can be an aluminum alloy.

A third subject of the invention is a method for neutron imaging immersed in a medium and using the leak-tight system of the invention characterized in that it comprises the following steps:
the immersion of said leak-tight system in a liquid medium comprising specimens to be analyzed;
the irradiation of said system by a flux of neutrons;
the removal of said system of said liquid medium;
the removal of said leak-tight vessel;
the recording of the scintillation generated by the second converter.

Advantageously, the object to be analyzed is not itself located directly within the liquid medium which can be water, but is introduced into a chamber, situated between the end of a collimator and the irradiation cassette. This chamber is filled with compressed air to purge the water.

According to one variant of the invention, the specimens to be analyzed are nuclear fuels, irradiated or not, in the case of neutronographic examinations performed prior to irradiation.

BRIEF DESCRIPTION OF THE DRAWINGS

The invention will be better understood and other advantages will become apparent upon reading the description that follows, presented by way of non-limiting example and thanks to the figures, amongst which are.

DETAILED DESCRIPTION

The present invention will be described in the framework of the analysis by neutron imaging of irradiating objects in a reactor fuel pond but could also be applied to the case of non-destructive testing of specimens immersed in a medium.

Figure 1:
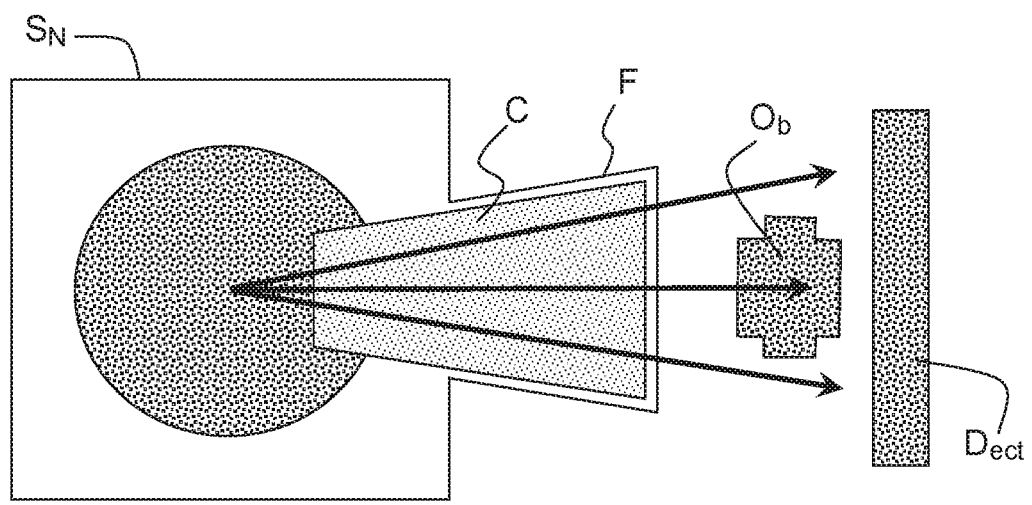
FIG. 1 illustrates a neutron imaging device according to the prior art.
Figure 2:
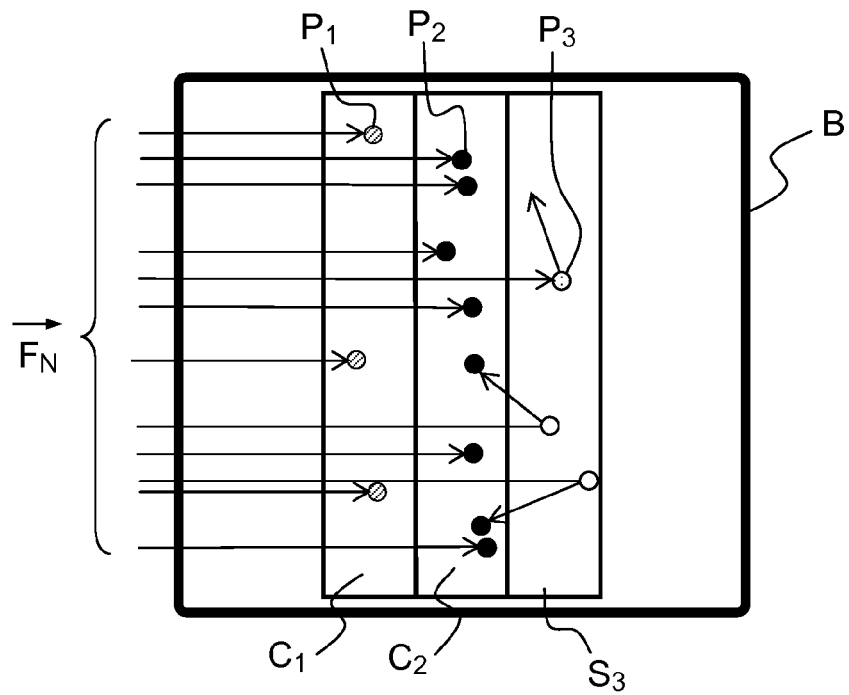
FIG. 2 illustrates a leak-tight system according to the invention and incorporating a first converter and a second converter.

FIG. 2 illustrates one example of a device used in the present invention and designed to be immersed in the pond of a reactor producing neutrons. The device comprises a first converter $C_1$ and a second converter $C_2$, in contact with the first converter. According to this example, the second converter is on the surface of a support $S_3$. When a flux of neutrons $F_N$ passes through the entirety of the device, it encounters neutron capture sites $P_1$ within the first material of the first converter, neutron capture sites $P_2$ in the second material of the second converter $C_2$ and neutron moderation sites $P_3$ within the material of the support $S_3$.

The material of the first converter is such that it is capable of generating a remnant β radiation with a decay time typically of a few hours.

The first converter is set into close contact with a second beta-light converter (scintillator) which furthermore possesses a strong neutron absorption. This second converter thus has a function that is three-fold:

when positioned in a reactor fuel pond in the irradiation cassette during the neutronographic irradiation, to reduce the activation of the cassette by the absorption of the residual thermal neutron flux having passed through the primary converter (around 85% of the flux); it is then used as a neutron shield for protection of the activatable structures situated upstream of the neutron flux (rear face of the irradiation cassette);

again during the neutronographic irradiation, to reduce the noise on the final image and thus to improve the quality of the image by the absorption of the spurious neutron flux originating from potential scattering events having taken place downstream of the primary converter;

once transferred outside of the pond and outside of the neutron flux, to supply a neutronographic image via the conversion of the beta radiation emitted by the activated primary converter and the recording of its scintillation signal. Its intimate contact with the primary converter allows an optimum uniformity and spatial resolution of the image to be ensured.

The primary converter and secondary converter assembly are furthermore applied on a transparent rigid support, the role of this transparent rigid support being three-fold:

to allow the assembly to be readily manipulated by providing a rigidity to the plate with large dimensions but of very limited thickness;

to reduce the impact of the activation of the irradiation cassette by the fast neutrons by moderating the fast neutrons via its hydrogenated compounds;

to ensure a reinforced biological protection during the handling of the assembly by the absorption of the residual beta radiation coming from the primary converter and without absorbing the light signal produced by the secondary converter.

The device thus formed is integrated into a leak-tight vessel B as illustrated in FIG. 2 in such a manner as to form a perfectly leak-tight system allowing the immersion of the assembly of the two converters without degradation and interaction with the immersion medium. The role of the leak-tight sealing is also to avoid the neutrons encountering water along their path between the start of the collimator and the converter, without which no correct image is possible. The following are therefore leak-tight and filled with gas (helium or air): the collimator, the chamber accommodating the object to be inspected and the cassette accommodating the converters.

In order to carry out the recording of the scintillation, the leak-tight vessel is removed from the immersion medium and the support and converters are taken out of it.

Figure 3:
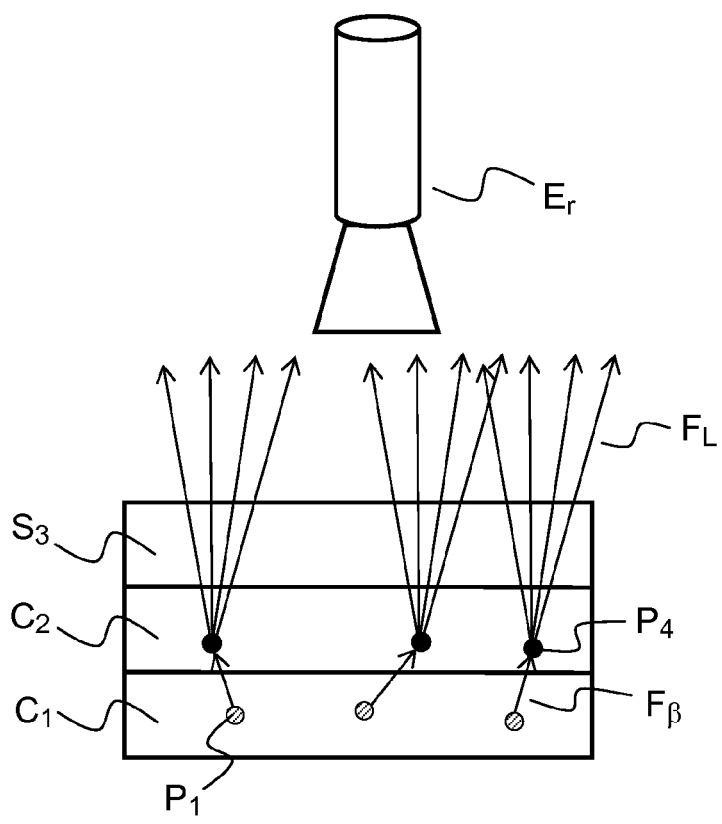
FIG. 3 illustrates a step for recording the scintillation produced by the second converter in a neutron imaging method according to the invention.

FIG. 3 illustrates the step for recording the scintillation by a device of the camera type $E_r$. The image is indeed produced by the recording of the scintillation produced by the secondary converter, said camera being positioned with a direct view of the surface of the transparent support covering the secondary converter, without having to make use of a system for reflecting the image, greatly simplifying this type of reading methods widely applied in neutronography by direct method which impose the use of a mirror (used for protecting the electronics of the camera from the residual neutron or gamma radiation by positioning it off-axis).

FIG. 3 shows the remnant beta radiation $F_\beta$, owing to the decay time of this radiation of several hours at the capture centers $P_1$, the transmission of this remnant beta radiation in turn allowing a light radiation $F_L$ to be generated at the scintillation centers $P_4$.

The first material of the first converter can be made of Dysprosium for example, and the thickness of the converter can be around 150 µm.

The second material of the second converter can comprise $Gd_2O_2S(Tb)$ (Gadox) mixed with an organic binder for example. The thickness of the second converter can be around 10 µm.

The transparent support can be composed of Plexiglas® (polymethylmethacrylate or PMMA) with a thickness of 5 mm.

The function of shielding the irradiation cassette and of absorbing scattered neutrons is thus provided both by the neutron-absorbing converter $C_2$ and the support $S_3$. The solution provided has the advantage of enabling the cost of the system to be reduced by the use of an element playing several roles, while at the same time avoiding the use of toxic neutron-absorbing materials (Cadmium) in contact with the operator.

Bringing the two converters and the rigid transparent hydrogenated support into close contact during the fabrication guarantees that a very good spatial resolution is obtained thanks to the reduced thickness needed for the secondary converter (around 10 µm, without the need for any additional superficial layer between the surfaces of the two converters). A gain of a factor 2 on the spatial resolution is thus achievable with respect to the current method allowing the best spatial resolution (transfer from a primary converter onto a thin X-ray film).

It also has the advantage of considerably reducing the duration of the measurement process by eliminating the need for bringing two elements into contact (use of vacuum box, etc.).

Furthermore, the capacity for absorption of the neutrons of the converter $C_2$ advantageously participates in the acquiring of an image of good quality by the elimination of the unwanted back-scattered neutrons from the rear of the device toward the converter $C_1$.

The use of a non-activatable transparent hydrogenated support advantageously allows the activation of the cassette to be reduced which would be due to the fast neutron reactions (nuclear activation reactions of the type (n,p) or (n,2n)) by thermalizing the fast part of the spectrum of the incident neutrons, which allows a neutron spectrum comprising neutrons of all energies to be used.

These reactions are reactions of the activation reaction types producing radioactive elements from incident fast neutrons and respectively corresponding to:

(n,p) the production of an isotope having an atomic number lower by 1, with conservation of the mass number;

(n,2n) the production of an isotope conserving the same atomic number, but with a mass number lower by 1;

These reactions only exist beyond a certain energy of the neutrons, the high-energy, fast neutrons.

The biological protection of the transparent hydrogenated support against beta radiation coming from the primary converter, after transfer outside of the pond, offers the possibility of handling that presents little or no radiation exposure for the operator.

The transparency of the hydrogenated support with respect to the scintillation light emitted by the secondary converter allows the entirety of the surface corresponding to the primary converter to be imaged directly, without having to use any complex optics and without requiring an additional digitization step as is the case in the methods currently used.

The invention claimed is:

1. A device designed to be used for neutron imaging immersed in a medium containing specimens to be analyzed, comprising: a first converter comprising a first material capable of converting thermal neutron radiation into remnant beta radiation by its neutron activation and a second converter comprising a second material capable of absorbing thermal neutron radiation by capture and capable of converting a remnant beta radiation into light radiation, said second converter being in contact with said first converter, and further comprising a support comprising hydrogenated species on which said second converter is positioned, said support being transparent to said light radiation.

2. The device designed to be used in neutron imaging as claimed in claim 1, wherein the first material comprises dysprosium.

3. The device designed to be used in neutron imaging as claimed in claim 1, wherein said second converter comprises a scintillator material which is a compound containing gadolinium, which can be of the type (Tb doped) $Gd_2O_2S$.

4. The device designed to be used in neutron imaging as claimed in claim 3, wherein the scintillator material is mixed with an organic binder.

5. The device designed to be used in neutron imaging as claimed in claim 1, wherein the thickness of the first converter is of the order of a hundred microns.

6. The device designed to be used in neutron imaging as claimed in claim 1, wherein the thickness of the second converter is of the of the order of ten microns.

7. The device designed to be used in neutron imaging as claimed in claim 1, wherein the support comprises a transparent material, with hydrogenated species, of the polymethylmethacrylate type, where said support can have a thickness of the order of a few millimeters.

8. A leak-tight system designed to be used in neutron imaging immersed in a medium comprising a device as claimed in claim 1 and a vessel leak-tight to said medium, incorporating the first converter, the second converter, and the support.

9. A method for neutron imaging immersed in a medium and using a system as claimed in claim 8, comprising:

immersing said system in a liquid medium comprising specimens to be analyzed;

irradiating said system by a flux of neutrons;

removing said system from said liquid medium;

removing said converters from said leak-tight vessel; and recording of the scintillation generated by the second converter.

10. The neutron imaging method as claimed in claim 9, wherein the specimens to be analyzed are nuclear fuels.

* * * * *